(12) United States Patent
Noble et al.

(10) Patent No.: US 10,687,945 B2
(45) Date of Patent: Jun. 23, 2020

(54) CHANNEL IMPLANT

(71) Applicant: Poriferous, LLC, Newnan, GA (US)

(72) Inventors: Aaron Noble, Newnan, GA (US);
Michael A. Burnstine, Pasadena, CA (US)

(73) Assignee: Poriferous, LLC, Newnan, GA (US)

( * ) Notice: Subject to any disclaimer, the term of this patent is extended or adjusted under 35 U.S.C. 154(b) by 77 days.

(21) Appl. No.: 15/881,136

(22) Filed: Jan. 26, 2018

(65) Prior Publication Data

US 2018/0206994 A1    Jul. 26, 2018

Related U.S. Application Data

(60) Provisional application No. 62/450,724, filed on Jan. 26, 2017, provisional application No. 62/549,112, filed on Aug. 23, 2017.

(51) Int. Cl.
*A61F 2/28* (2006.01)
*A61F 2/30* (2006.01)
*A61L 27/12* (2006.01)
*A61B 17/84* (2006.01)

(52) U.S. Cl.
CPC .......... *A61F 2/2875* (2013.01); *A61F 2/2846* (2013.01); *A61B 17/842* (2013.01); *A61F 2002/2835* (2013.01); *A61F 2002/2878* (2013.01); *A61F 2002/3008* (2013.01); *A61F 2002/30011* (2013.01); *A61F 2002/3092* (2013.01); *A61F 2002/3096* (2013.01); *A61F 2002/30576* (2013.01); *A61F 2002/30578* (2013.01); *A61F 2002/30968* (2013.01);
(Continued)

(58) Field of Classification Search
CPC ............ A61F 2/2875; A61F 2002/2878; A61F 2/2846; A61F 2002/2835
See application file for complete search history.

(56) References Cited

U.S. PATENT DOCUMENTS

| | | | |
|---|---|---|---|
| 6,787,216 B1 * | 9/2004 | Koenhen .............. | B01D 63/066 156/244.13 |
| 2006/0224242 A1 * | 10/2006 | Swords .............. | A61B 17/8085 623/17.19 |
| 2014/0052264 A1 | 2/2014 | Hufen et al. | |

(Continued)

FOREIGN PATENT DOCUMENTS

WO        2004093743 A1    11/2004

OTHER PUBLICATIONS

International Search Report and Written Opinion, PCT Patent Application No. PCT/US2018/015411, dated May 15, 2018, 11 pages.

(Continued)

*Primary Examiner* — Brian A Dukert
*Assistant Examiner* — Rebecca Lynee Zimmerman
(74) *Attorney, Agent, or Firm* — Kilpatrick Townsend & Stockton LLP

(57) ABSTRACT

Embodiments relate generally to channel implants used for surgical reconstruction and/or repair. Certain embodiments of the channel implants are designed for craniofacial surgery, reconstruction, and/or augmentation. More specifically, some embodiments find particular use in orbital reconstructive surgery, such as repair of the orbital floor or supraorbital ridge (brow ridge). Embodiments also relate to methods for using and for manufacturing the channel implants disclosed.

16 Claims, 7 Drawing Sheets

(52) U.S. Cl.
CPC .............. *A61F 2002/30971* (2013.01); *A61F 2310/00023* (2013.01); *A61L 27/12* (2013.01)

(56) References Cited

U.S. PATENT DOCUMENTS

2015/0320561 A1* 11/2015 Noble ..................... A61F 2/28
623/17.18
2016/0367393 A1 12/2016 You

OTHER PUBLICATIONS

PCT Patent Application No. PCT/US2018/015411, International Preliminary Report on Patentability, dated Aug. 8, 2019, 8 pages.

* cited by examiner

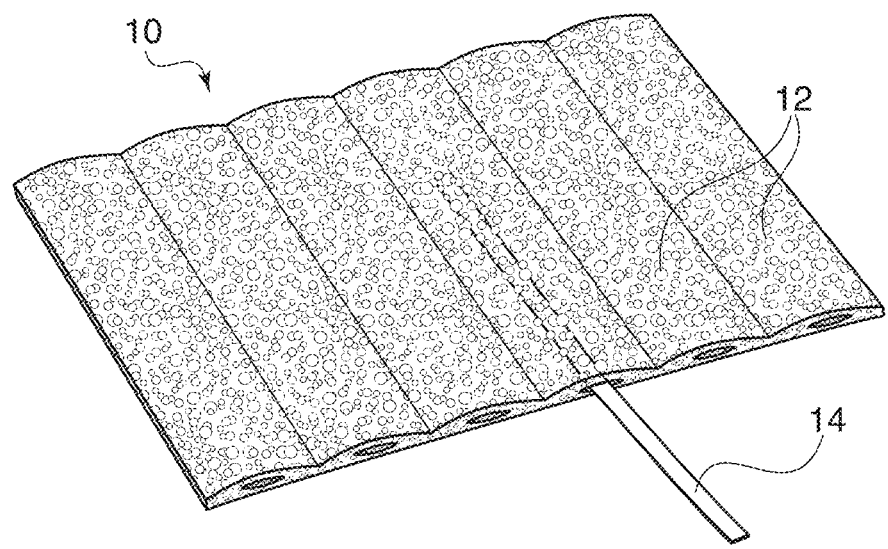
FIG. 3 *(Prior Art)*
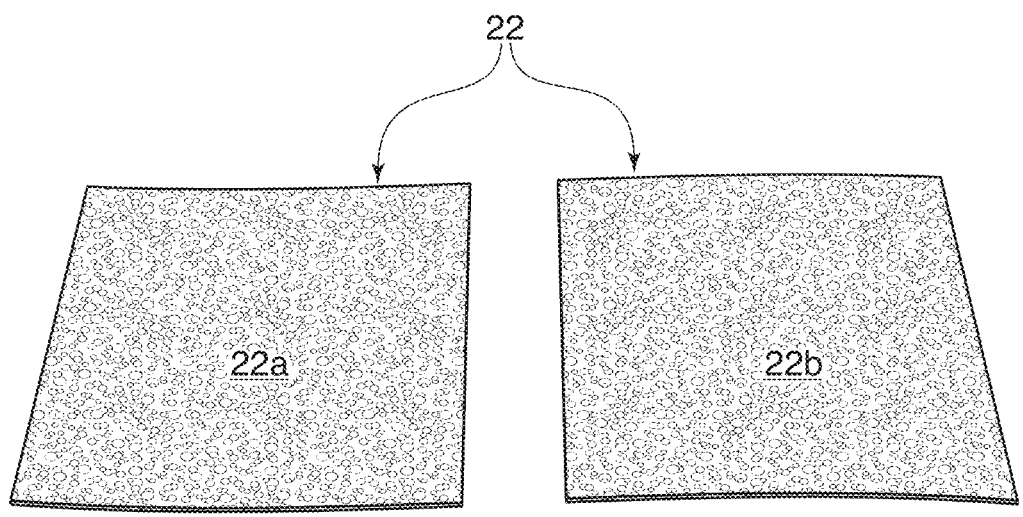
FIG. 4

CHANNEL IMPLANT

CROSS REFERENCE TO RELATED APPLICATIONS

This application claims the benefit of U.S. Provisional Application Ser. No. 62/450,724, filed Jan. 26, 2017, titled "Significantly Thin Orbital Floor Implant with Channel," and U.S. Provisional Application Ser. No. 62/549,112, filed Aug. 23, 2017, titled "Micro Channeled Porous Sheet," the entire contents of each of which are hereby incorporated by reference.

FIELD OF THE DISCLOSURE

Embodiments of the present disclosure relate generally to channel implants used for surgical reconstruction and/or repair. Certain embodiments of the channel implants are designed for craniofacial surgery, reconstruction, and/or augmentation. More specifically, some embodiments find particular use in orbital reconstructive surgery, such as repair of the orbital floor or supraorbital ridge (brow ridge). Embodiments also relate to methods for using and for manufacturing the channel implants disclosed.

BACKGROUND

The orbit is the boney socket in the skull that contains and houses the eye, along with the associated structures that support eye function, such as the eye muscles, nerves, and blood vessels. In some instances, a variety of problems can occur in the eye socket, ranging from inflammatory diseases or other diseases, tumors, infections, birth defects, or injuries from trauma. When these problems occur, it may become necessary to reconstruct various portions of the orbital socket, including the orbital floor and/or the supraorbital ridge.

Advances in bone and surgical technology have provided materials that may serve as a substitute for the patient's own tissue, when needed. These advances include titanium plates and screws, hydroxyapatite cement, porous polyethylene, and resorbable fixation devices. However, improvements to surgical implants and materials are desirable.

BRIEF SUMMARY

Embodiments of the invention described herein thus provide systems and methods for improved channel implants. Embodiments of the implants may include In one example, there is provided a channel implant, comprising two porous sheets of material, each porous sheet of material having a thickness that is less than or equal to two particles thick; and a channel formed between the two porous sheets of material, the channel configured for fixation plate insertion, wherein the resulting channel implant has a thickness less than about 1.75 mm. The channel implant may have a uniform thickness.

In some examples, it is possible to provide a membrane layer on a top surface, on a bottom surface, or on both top and bottom surfaces of the channel implant. This can change the porosity of the implant body. In other examples, the channel can be less porous than remaining body portions of the channel implant.

The channel implant may be manufactured by laminating the two porous sheets of material with a removable mold core inserted during lamination. For example, the implant may be manufactured by: manufacturing or obtaining first and second porous sheets of material, each porous sheet of material have a thickness that is less than or equal to two particles thick; positioning the first porous sheet of material in a mold; positioning a mold core on the first porous sheet of material; positioning the second porous sheet of material over the first porous sheet of material and the mold core to form an assembled structure; thermally processing the assembled structure; removing the thermally processed assembled structure from the mold; and removing the mold core from between the two porous sheet of material to reflect a channel therebetween.

The channel implant may have a thickness of about 1.75 mm to 1.0 mm. Other versions provide a thickness of about 1.5 to 0.85 mm. Further versions provide a thickness of about 1.0 to 0.5 mm.

The channel implant may have multiple channels. The one or more channels may extend only partially across an implant width or length. In other examples, the channel extends the entire width or length of the implant body. There may be pre-installed lengths of malleable metal through the one or more channels. The malleable metal generally extends out from the implant. The malleable metal may comprise at least one fixation hole. In other examples, there may be one or more radio opaque strips of material pre-installed. In further examples, the channel is configured to receive suture material therein.

BRIEF DESCRIPTION OF THE DRAWINGS

FIG. 3 shows a top perspective view of the prior art channel implant of FIG. 1 with the fixation plate in position in one of the channels.

FIG. 4 shows sheet materials used for manufacturing of a channel implant.

DETAILED DESCRIPTION

Embodiments of the present invention provide channel implants that are designed for repair of the orbital floor and wall trauma (or damage/trauma to surrounding bones, i.e., the brow bone ridge). The implants may be used where the addition of one or more rigid fixation plates are needed to offer structural support. In some examples, the implant may be cut to the desired shape.

Figure 1:
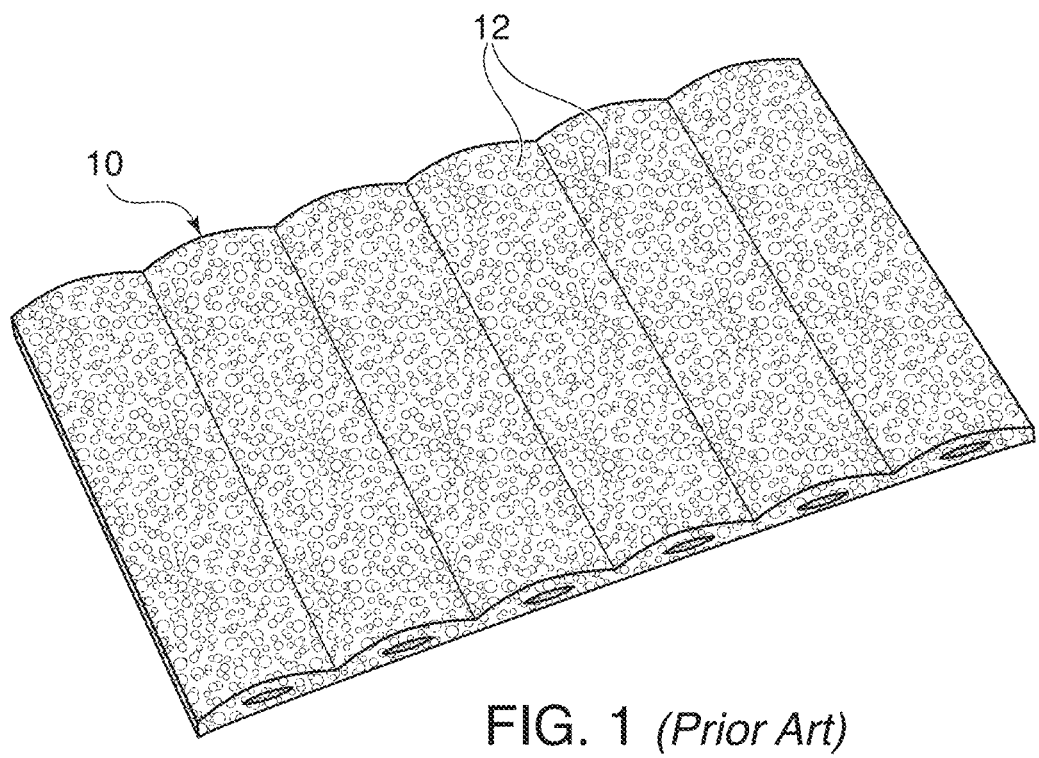
FIG. 1 shows a top perspective view of a prior art channel implant.
Figure 7A:
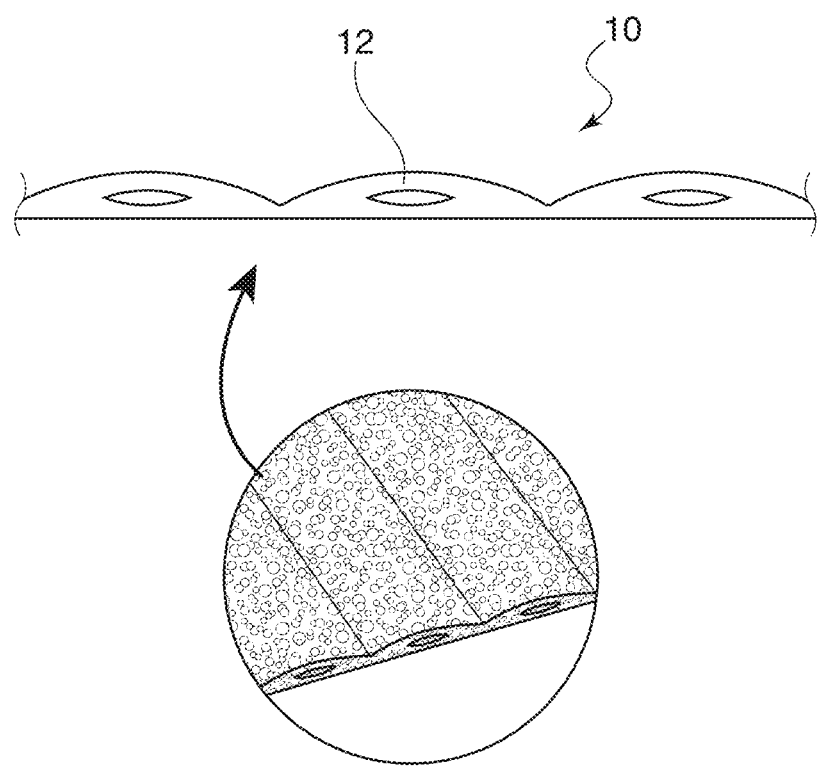
FIG. 7A shows a side cross-sectional schematic view of a prior art channel implant. This shows the current technology where the porous structure is thicker surrounding the channel.

For prior implants, after the implant has been cut to shape, a fixation plate is inserted into a channel formed in the implant body. Examples are illustrated by FIGS. 1 and 3. In these examples, the implant 10 has a series of channels 12 that have been pre-formed into the implant. This is illustrated by prior art FIG. 1. The fixation plate may 14 is then inserted through one of the channels 12. The fixation plate 14 can extend out both ends of the implant if desired, as shown by FIG. 3. This figure illustrates the thickness needed to form a channel while providing enough thickness for manufacturing (e.g., to allow the mold to fill with material for formation). This results in the illustrated bulge in the implant, at the location of the channel. This can be seen even more clearly in the prior art images at FIG. 7A. The bulge created by channel formation is undesirable and is only tolerated due to the current limits of manufacturing know how.

Providing a plate 14 through the channel 12 allows the surgeon to bend and contour the implant to the desired shape. Once the implant shape and proper positioning have been determined, the end of the fixation plate 14 is fixed to the orbital rim/bone.

One challenge with prior channel implants has been their overall thickness, particularly at the channel bulge, which has generally been dictated due to the manufacturing techniques and formation of channels within the implant. As background, channel implants currently available on the market have a thickness of material surrounding the channel that is required to be thick enough to allow particles of material to fill into a mold cavity with a central located core. After thermal processing, the formed porous article is removed from the mold. Then upon removing the core by pulling the core therefrom, a porous implant is formed having a channel to receive a fixation plate. The limitation of this technology is that it requires a significant thickness surrounding the channel.

However, when implants are intended for use in delicate craniofacial applications, the present inventors have determined that it is desirable to develop and use a channel implant that is thinner than those currently provided. Accordingly, the present inventors have developed an implant for use in craniofacial applications that is substantially thin, being thinner than currently available products on the market. Thin implants are desirable as they do not overlift lift the eye following placement into the orbital floor. For comparison, the implant of FIGS. 1 and 3 is about 2.0-2.5 mm. By contrast, the implants disclosed herein have a thickness that can range from about 1.75 mm or less at the channel portion.

More specifically, the channel implants, including the fixation plate, have a total implant thickness that ranges from about 1.75 mm to 1.0 mm. In other examples, the porous implant has a thickness that ranges from 1.5 to 0.85 mm. In other examples, the porous implant has a thickness that ranges from 1.0 to 0.5 mm. In a specific example, the channel implants can be about 0.45 mm thick. In specific examples, an implant manufactured for particular use in the orbital floor can be 0.45 mm thick with a channel 28 for receiving a fixation plate 14. In other examples, orbital floor embodiments having uniform thicknesses of 0.85 mm, 1.0 mm, 1.5 mm or 1.6 mm are possible. (This is in contrast to current channel implants, which have a 2.3 mm thick bulge area around the channel.) The channel portions may be about 0.25, 0.50, 0.85, 1.0 thick by about 2.3-about 4.0 mm wide, depending upon particular design constraints implemented. An implant manufactured for particular use for placement via suture (described further below) can be a suture channel implant that is a uniform 0.45 mm thick structure with a microchannel 32 provided for receiving a suture. The suture channel portion may be about 0.25 mm thick by about 0.75 mm wide.

Figure 7B:
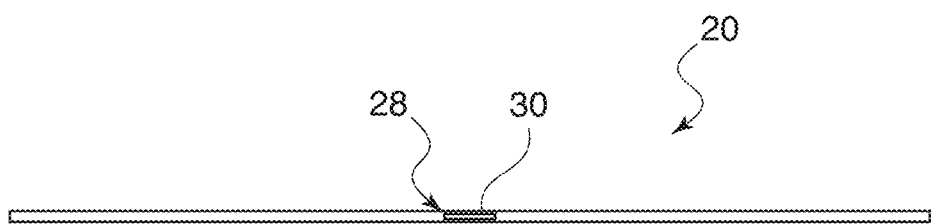
FIG. 7B shows a side cross-sectional schematic view of a channel implant made according to this disclosure. The implant compress the two layers of material so that thickness of the implant is maintained as being generally uniform. There is not a bulge provided as with the prior art channel implants.

The methods used for manufacturing the channel implants disclosed allows them to have a uniform thickness, meaning that the bulge of the prior art channel implants is eliminated. As illustrated by FIG. 7B, the cross-sectional view of the implant reflects that the thickness does not change (at least not substantially) at the channel portion 28.

The general intent is to provide an implant that is much thinner than current technology. This may be done by manufacturing a thin orbital sheet as the base material for the channel implant. Examples of manufacturing methods and orbital sheets that may be used in connection with the channel implants disclosed herein are described in Applicant's U.S. Pat. No. 9,724,198 titled "Orbital Floor Sheet," the entire contents of which are incorporated here by reference.

As outlined in that patent, one way to manufacture orbital floor sheets may be to form a thin porous sheet on a heated mandrel. The porous sheet that is formed generally has an interconnected pore structure that may be compressed by heat compression without losing porosity. In many examples, the sheet is only about one to two particles thick. The interconnected pore structure may be an open pore structure with a pore volume that ranges from about 10 to 50%. Additional membrane materials or other layer materials may be applied to one of the face surfaces of the porous sheet and/or to one of the edge surfaces of the porous sheet.

Figure 2:
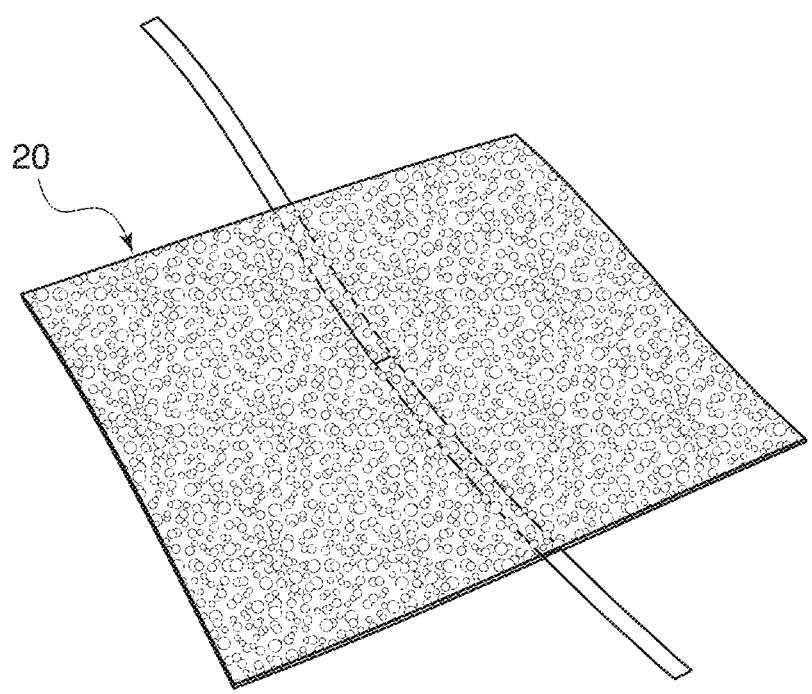
FIG. 2 shows a top perspective view of one embodiment of a channel implant described herein.

Side-by-side images illustrated by FIGS. 1 and 2 show a prior art channel implant (FIG. 1) as compared to the channel implant 20 described herein (FIG. 2). Unlike traditional channel implants, the channel implant technology described herein allows the channel to be formed so that the thickness of material surrounding the channel is less than the thickness of the material particle size. In other words, there are thinner walls on either side of the "channel" that what can be accomplished with traditional molding technology.

As illustrated by FIG. 4, in order to manufacture the channel implant 20, two layers or pieces of sheet material 22 are provided. The sheet material 22 generally has one or more features described by U.S. Pat. No. 9,724,198 titled "Orbital Floor Sheet." The sheet material 22 may be manufactured as described therein. In one example, the sheets 22 have open pores and are formed on a heated mandrel and harvested, resulting in a sheet having a thickness of less than (or about) two particles thick. During manufacturing in a mold cavity, a mold core 24 with mold release functionality is positioned between two portions of sheet material 22 in order to create the channel. When the mold core 24 is removed, a thin channel results.

Figure 5:
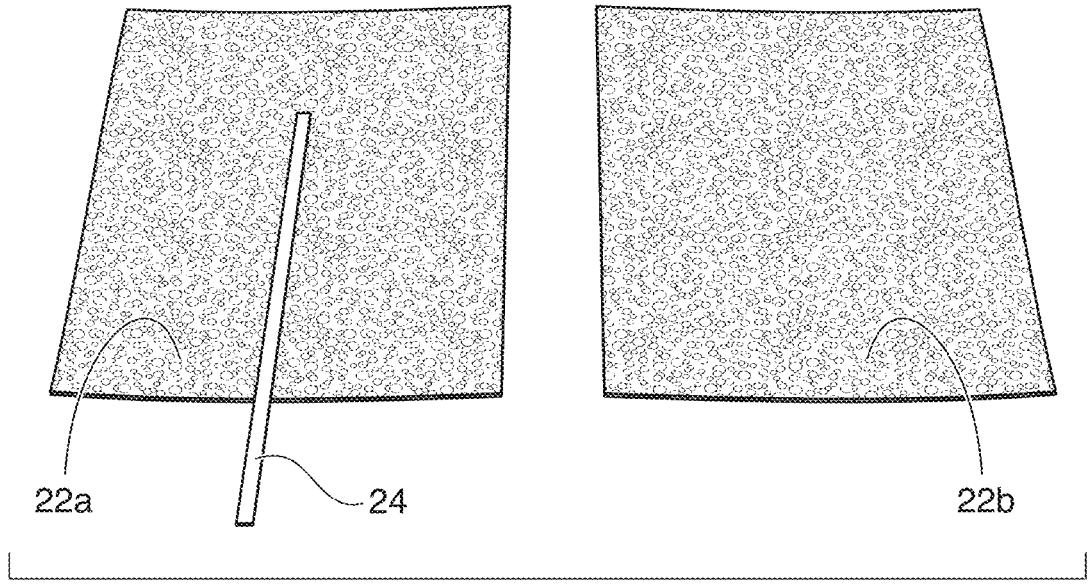
FIG. 5 shows a mold core in place on one of the sheet materials of FIG. 4.
Figure 6:
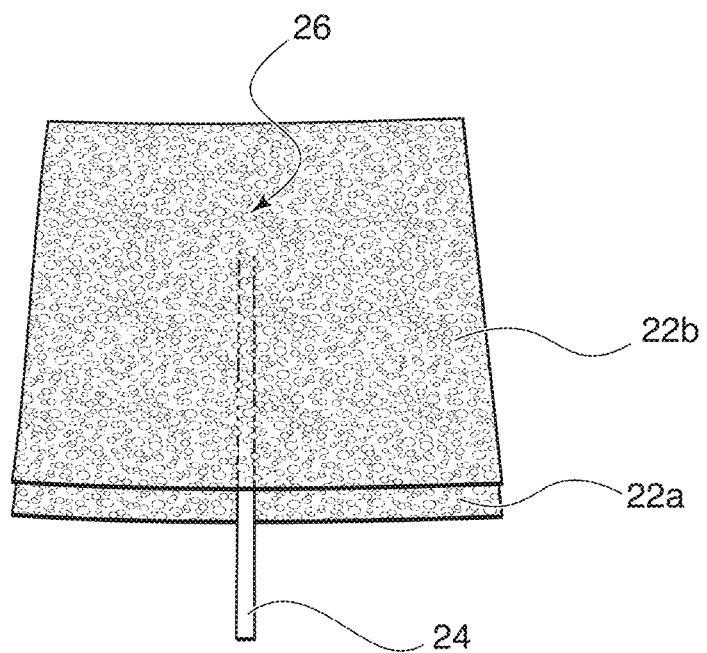
FIG. 6 shows a laminated or assembled structure of a channel implant prior to thermal processing.
Figure 8A:
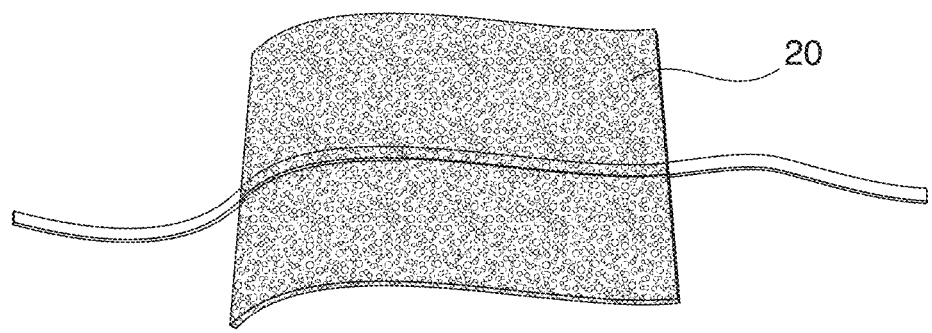
FIG. 8A shows the laminated or assembled structure of FIG. 6 after thermal processing, with a fixation plate positioned partially through the channel (illustrated as extending from the left side of the implant). A strip of paper is extended through the remaining portion of the channel and is seen extending from the right side of the implant.
Figure 8B:
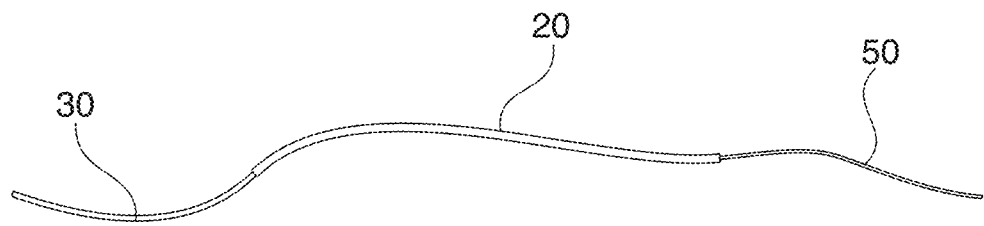
FIG. 8B shows a side plan view of the implant of FIG. 8A This view illustrates the significant thinness of the channel implant from a side view. The metal plate represents the insertion of a fixation plate at the left side of the implant. The strip of paper extending from the right side of the implant represents an embodiment in which the channel passes all the way through the implant. This image also shows how the inserted fixation plate, when bent, is mechanically locked into the assembly, providing mechanical entrapment once bent, and preventing the plate from being pulled out of the channel.

A specific example of a manufacturing process is described below. It should be understood, however, that this is only one example that may be used to manufacture a channel implant 20 with substantially thin walls on either side of the channel. Other variations are possible and considered within the scope of this disclosure. In one example, the steps are:

1. A sheet with open pores is formed on a heated mandrel and harvested, resulting in a sheet (22) having a thickness of less than two particles thick.
2. One thin sheet 22a is positioned on to a mold cavity surface. (See FIG. 4.)
3. A thin mold core 24, made from thin flexible material with mold releasing function, is placed on top of the sheet 22a in a desired location relative to the pattern of sheet and the desired location of channel. (See FIG. 5.)
4. A second sheet 22b (formed via step 1) is placed on top of the thin mold core 24, which forms a lamination or assembled structure 26. (See FIG. 6.)
5. The mold cavity is closed, with closure being of a desired thickness (generally less than 1.75 mm thick)
6. The mold (containing the implant assembled structure 26) is thermally processed with heat and, pressure sintering the particles of the 22a and 22b sheets together around the thin core 24.
7. After cooling, the porous article, now formed structure 20, is removed from the mold and the thin core 24 is pulled out, leaving a formed channel 28. (See FIGS. 7B and 8A.)
8. A fixation plate 30 may be inserted into the formed channel 28 (See FIGS. 8A and 8B.) These figures show both the fixation plate 30 and a paper strip 50 used to represent the remaining portion of the channel. The fixation plate 30 is the metal component on the left side of the image and the paper strip 50 extends on the right side of the implant. FIG. 8B shows a simulated fixation plate 30 inserted and bent into the desired shape, which causes the porous body of the channel implant 20 to follow the shape of the fixation plate.
9. The formed channel implant 20 is then trimmed to the desired shape respective to the position of the channel's designed location.

During formation of the channel implant, it is possible that some areas may become more compressed and others. In a specific example, the channel itself may go solid (e.g., lose some or all of its porosity) during formation/thermal treatment. This has been found to be a potential benefit to the channel implant. For example, a solid channel can provide additional strength to the implant, whereas porous channels may be susceptible to break down. In most instances, it remains desirable that the body of the channel implant remain porous. However, it is possible to provide post-treatment or additional layers that can reduce minimize or altogether eliminate any porous surfaces.

Figure 9:
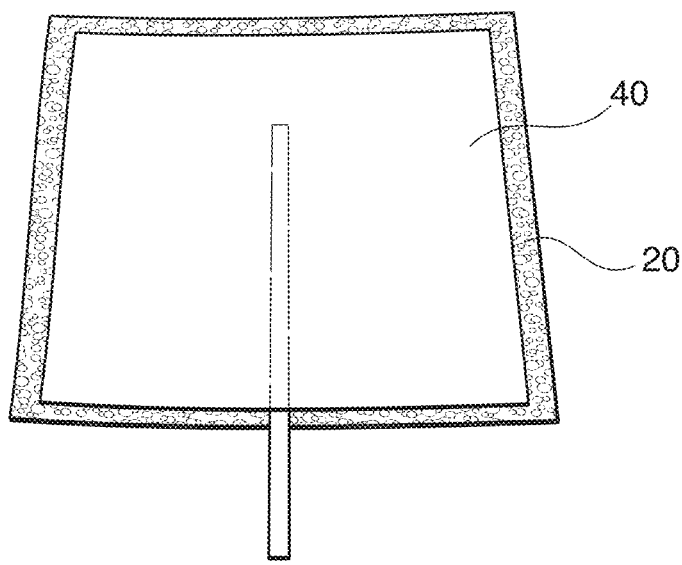
FIG. 9 shows a thermally processed channel implant with a membrane positioned on one of its outer surfaces.

For example, is possible to provide a solid membrane layer 40 (generally comprised of the same polymer as the sheet material 22) that can be added to one or both sides for implants where targeted tissue integration is required. One example is illustrated by FIG. 9. As used herein, the term "solid membrane layer" is intended to refer to a layer that is generally non-porous or that otherwise does not allow tissue integration therethrough.

Although a single fixation plate 30 is shown, it should be understood that the channel implant 20 can be pre-assembled with one or multiple metal bars installed into the channels allowing for bending into shape.

It should also be understood that the metal fixation plates may typically have one or multiple holes for receiving fixation screws for positioning the implant in place with respect to a patient's bone.

Additionally or alternatively, the channel implant 20 can be pre-assembled with one or multiple radio opaque strips into the channels allowing for identification of implant position on MRI imaging.

In an alternate embodiment, it is possible to limit the length of the channel, such that it does not extend through the entire width or length of the implant body. In other words, the channel can be open from one edge, but not extend all the way through. This can help to limit the depth of the inserted plate. Such an embodiment can be useful to help direct the proper orientation of the implant while providing a safety feature (in order to avoid certain targeted features). For example, in this embodiment, the plate cannot extend out the back of the implant, which prevents it from damaging the optic nerve. This also provides an indicator to the surgeon that the "front" of the implant has the open channel and the "back" of the implant does not have a channel or otherwise has a closed channel. More generally, this embodiment can be useful when the plate should not be permitted to extend deeper than desired.

Microchannel for Temporal Brow Lift

In some examples, the channel may be manufactured to be a microchannel 32. In one set of testing, the microchannel embodiment has been found to be particularly useful as a temporal brow lift implant. This implant may be manufactured as described above, but with use of a thinner mold core. For example, the mold core may approximate the dimensions of suture material, rather than a fixation plate strip.

As background, certain eyebrow implants developed in the past have failed to adequately lift the supporting facial structures. Suture, barbed sutures, and filler products have been used to elevate and fill the eyebrow, but over time, tissue descent recurs with these different suture products. Similarly, soft tissue fillers tend to be temporary, have variable effect on tissue elevation, and need to be repeated.

The microchannel brow lift embodiment can used to lift and support facial structures and may be referred to as a temporal brow implant. Aging changes in facial structures include bone loss, tissue descent, and tissue (fat) volume loss. Methods to lift and correct the facial aging changes have been developed. These include implant onlays or bone grafting for bone augmentation; lifting tissue for gravitational facial descent; and volume augmentation with various autologous, bioengineered, and tissue stimulating products for volume loss. The temporal brow implant was developed with the intent to lift tissue and augment volume (fill) by the lift the eyebrow (although various designs and shapes can be used for different parts of the face for facial support). The implant is placed deep into the facial fat pad and elevates the fat pad by anchoring it to a deep superior fascial tissue plane. This vertically elevates the tissue and adds volume through tissue recruitment. The temporal brow lift implant functions similarly to a bra to support the fat pads in the face (the retroorbicularis oculi fat (ROOF) pad).

Figure 10:
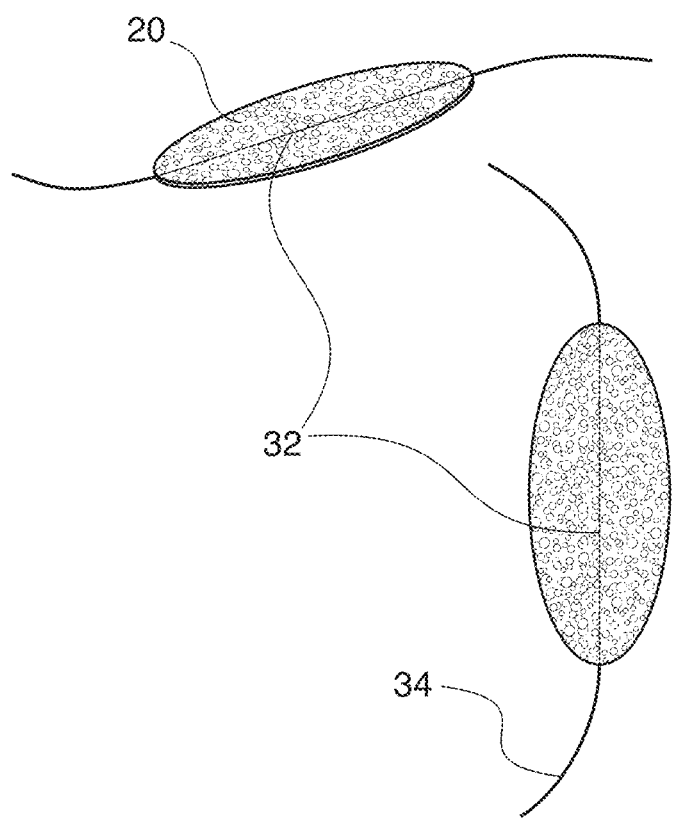
FIG. 10 shows a channel implant configured for use with suture material.

In the microchannel brow lift example, the microchannel 32 is configured to receive suture material 34 and has dimensions that are sized accordingly. In use, the microchannel 32 is formed into porous implant sheet having substantially thin cross section. (In this specific example, the resulting implant sheet is about 0.45 mm thick). Suture material 34 can be then threaded through the microchannel 32, as illustrated by FIG. 10. This provides a channel implant 20 that can be used to suspend tissue, such functions as are performed during face lift surgery. The porous sheet of the channel implant 20 provides an area of tissue integration, spreading the forces of the suture over the porous area. This can help prevent the suture from pulling through the tissue when under load.

Figure 11:
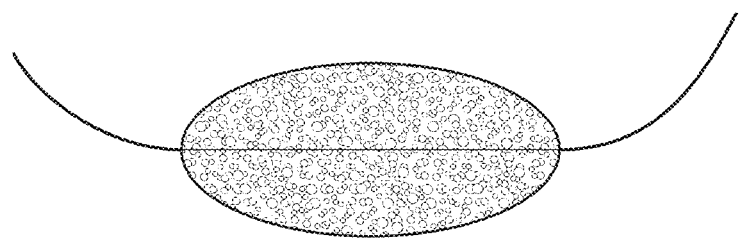
FIG. 11 shows a first schematic illustration of use of the channel implant of FIG. 10.
Figure 12:
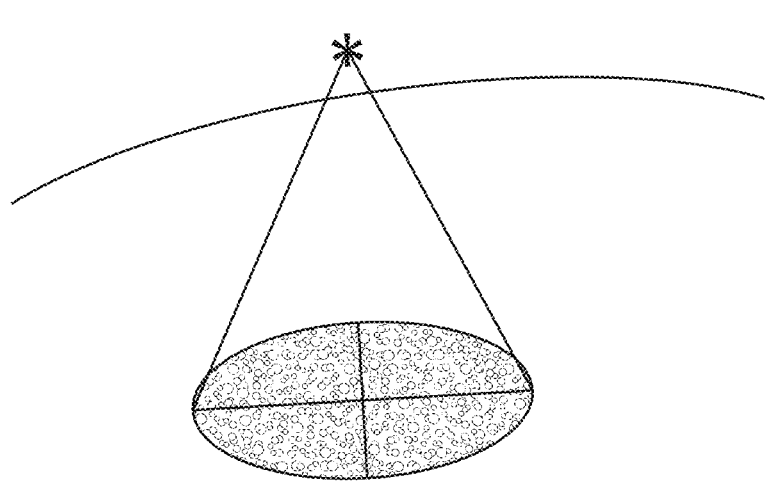
FIG. 12 shows a second schematic illustration of use of the channel implant of FIG. 10.

The channel implant 20 can be implanted when performing an upper blepharoplasty or can be placed with a small subbrow incision. It lifts the tail of the eyebrow and augments lateral brow volume by suspension to the temporalis fascia. Sketches of forces and implantation are illustrated by FIGS. 11 and 12.

Although the implants described herein are generally described and illustrated with respect to flat sheets, it should be understood that channel implants may be designed according to this disclosure in various three-dimensional shapes as well. A combination of mold shapes and/or core inserts may be used in order to provide various other implant shapes having a channel running fully or partially therethrough.

Changes and modifications, additions and deletions may be made to the structures and methods recited above and shown in the drawings without departing from the scope or spirit of the disclosure or the following claims.

What is claimed is:

1. A channel implant used for surgical reconstruction and/or repair, comprising two porous sheets of material; and a channel formed between the two porous sheets of material, the channel configured for fixation plate insertion, the porosity of the two porous sheets of material changing to non-porous along at least some areas of the channel during thermal processing of the sheets with heat and pressure, forming an at least partially non-porous channel; wherein the resulting channel implant has a substantially uniform cross-sectional thickness along the channel implant that is 1.75 mm or less.

2. The channel implant of claim 1, further comprising a membrane layer on a top surface, on a bottom surface, or on both top and bottom surfaces of the channel implant.

3. The channel implant of claim 1, manufactured by laminating the two porous sheets of material with a removable mold core inserted during lamination.

4. The channel implant of claim 1, having multiple channels.

5. The channel implant of claim 1, having a thickness of about 1.75 mm to 1.0 mm.

6. The channel implant of claim 1, having a thickness of about 1.5 to 0.85 mm.

7. The channel implant of claim 1, having a thickness of about 1.0 to 0.5 mm.

8. The channel implant of claim 1, having pre-installed lengths of malleable metal.

9. The channel implant of claim 8, wherein malleable metal extends out from the implant.

10. The channel implant of claim 9, wherein the malleable metal comprises at least one fixation hole.

11. The channel implant of claim 1, comprising one or more radio opaque strips of material pre-installed.

12. The channel implant of claim 1, wherein the channel is configured to receive suture material therein.

13. The channel implant of claim 1, wherein the channel extends only partially across an implant width or length.

14. A method for manufacturing the porous channel implant used for surgical reconstruction and/or repair of claim 1, comprising: manufacturing or obtaining first and second porous sheets of material;
    positioning the first porous sheet of material n a mold;
    positioning a mold core on the first porous sheet of materia;
    positioning the second porous sheet of material over the first porous sheet of material and the mold core to form an assembled structure;
    thermally processing the assembled structure;
    the porosity of the two porous sheets of material changing to non-porous along at least some areas of the channel during thermal processing of the sheets with heat and pressure, forming an at least partially non-porous channel;
    removing the thermally processed assembled structure from the mold;
    and removing the mold core from between the two porous sheet of material to reflect a channel therebetween;
    wherein the resulting channel implant has a substantially uniform cross-sectional thickness along the channel implant that is 1.75 mm or less.

15. The method of claim 14, further comprising positioning a fixation plate, a radio opaque strip, or a suture material within the channel.

16. The method of claim 14, further comprising positioning more than one mold core on the first porous sheet of material in order to form more than one channel.

* * * * *